United States Patent
Ichinohe

(10) Patent No.: US 7,413,744 B2
(45) Date of Patent: Aug. 19, 2008

(54) COSMETIC PREPARATION

(75) Inventor: Shoji Ichinohe, Gunma (JP)

(73) Assignee: Shin-Etsu Chemical Co., Ltd., Chiyoda-Ku (JP)

( * ) Notice: Subject to any disclaimer, the term of this patent is extended or adjusted under 35 U.S.C. 154(b) by 259 days.

(21) Appl. No.: 10/559,928

(22) PCT Filed: Jun. 10, 2003

(86) PCT No.: PCT/JP03/07371

§ 371 (c)(1),
(2), (4) Date: Dec. 8, 2005

(87) PCT Pub. No.: WO2004/110393

PCT Pub. Date: Dec. 23, 2004

(65) Prior Publication Data

US 2006/0128882 A1    Jun. 15, 2006

(51) Int. Cl.
*A61K 8/00* (2006.01)
(52) U.S. Cl. .......................... 424/401; 524/268; 528/29
(58) Field of Classification Search ........................ None
See application file for complete search history.

(56) References Cited

U.S. PATENT DOCUMENTS

| | | | | |
|---|---|---|---|---|
| 4,301,268 A | * | 11/1981 | Kropac | 528/26 |
| 4,725,658 A | | 2/1988 | Thayer et al. | |
| 5,061,481 A | | 10/1991 | Suzuki et al. | |
| 5,417,967 A | * | 5/1995 | Kawamata et al. | 424/78.03 |
| 6,057,033 A | * | 5/2000 | Bilodeau | 428/372 |
| 2004/0071741 A1 | | 4/2004 | Derian | |

FOREIGN PATENT DOCUMENTS

| JP | 62-292867 A | 12/1987 |
|---|---|---|
| JP | 2-132141 A | 5/1990 |
| JP | 10-500431 A | 1/1998 |

* cited by examiner

*Primary Examiner*—Marc S Zimmer
(74) *Attorney, Agent, or Firm*—Birch, Stewart, Kolasch & Birch, LLP

(57) ABSTRACT

A cosmetic comprising the organopolysiloxane wax represented by the following formula (1),

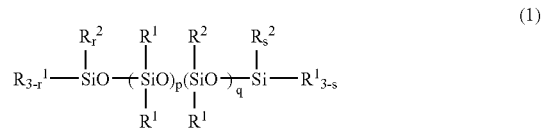
(1)

wherein $R^1$ is a group selected from the group consisting of alkyl groups having 1 to 20 carbon atoms, alicyclic groups, aryl groups, aralkyl groups and fluorinated alkyl groups;
$R^2$ is a group having a pentaerythritol higher fatty acid polyester residue represented by the following formula (2), $$(CH_2OCOR^8)_mC(CH_2O\text{—}X\text{—})_{4-m} \quad (2)$$

wherein $1 \leq m < 4$
or a group having a dipentaerythritol higher fatty acid polyester residue represented by the following formula (3), $$O(CH_2C)_2(CH_2OCOR^8)_n(CH_2O\text{—}X\text{—})_{6-n} \quad (3)$$

wherein $1 \leq n < 6$,
$R^8$ in the formulae (2) and (3) being a linear, saturated or unsaturated, aliphatic group having 17 to 30 carbon atoms,
—X— in the formulae (2) and (3) being anyone of the following moieties,

—$R^3$—,

—$COR^4$—, wherein $R^3$ is a $C_3$-$C_8$ alkylene group or a cycloalkylene group, $R^4$ is a $C_4$-$C_{20}$ aliphatic or alicyclic group having at least one group selected from the group consisting of carboxyl, carbonyloxy and hydroxyl groups,
p, q, r and s each is a number with $0 \leq p \leq 200$, $0 \leq q \leq 200$, $0 \leq r \leq 3$, and $0 \leq s \leq 3$, provided that $0 \leq p+q \leq 200$ and $1 \leq q+r+s$.

24 Claims, No Drawings

COSMETIC PREPARATION

FIELD OF THE INVENTION

The present invention relates to a cosmetic preparation, particularly to a cosmetic preparation which comprises organopolysiloxane wax modified with (di)pentaerythritol higher fatty acid ester to have excellent spreadability and sensory properties.

DESCRIPTION OF THE PRIOR ART

Silicone oils are used in various cosmetics because of their excellent properties. For example, they provide refreshing feel and spread smoothly. However, the silicone oils generally have bad compatibility with other kinds of unctuous agents used in cosmetics. Particularly when the silicone oils are used in cosmetics in the form of solid or stick, it is difficult to prepare cosmetics having good spreadability and sensory properties.

To make stable solid or stick-shaped cosmetics from silicone oils, a silicone oil is mixed with a modified silicone. Published Japanese Translation of International Patent Application No. 10-500431 describes a modified silicone having a functional group derived from analiphatic alcohol having 21 to 30 carbon atoms or behenate. Japanese Patent Application Laid-Open No.2-132141 describes an acryl-silicone graft copolymer.

However, it is difficult to prepare a lubricious solid or stick-shaped cosmetic from the compound described in Published Japanese Translation of International Patent Application No. 10-500431. A liquid unctuous agent such as ester oil, triglyceride oil, or paraffin oil is needed in the cosmetic to attain desired lubricity. The addition of the liquid unctuous agent is not necessary for the acryl-silicone graft copolymer. However, the acryl-silicone graft copolymer itself is resinous to damage lubricity of the cosmetic.

The present inventor have made research to make a lubricious solid or stick-shaped cosmetic without using a liquid unctuous agent and found that good results can be obtained by incorporating an organopolysiloxane wax modified with an ester of a $C_{18}$ or higher fatty acid with (di)pentaerythritol in a cosmetic containing a silicone oil.

SUMMARY OF THE INVENTION

The present invention is a cosmetic comprising an organopolysiloxane wax represented by the following formula (1).

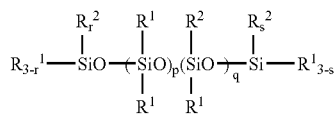
(1)

Preferably, the silicone wax has a weight average molecular weight, reduced to polystyrene, of from 1,000 to 8,000.

The present cosmetic preferably comprises a silicone oil (a) which is liquid at 25° C. in addition to the aforesaid organopolysiloxane was.

Preferably, the silicone oil (a) is at least one selected from the group consisting of linear organopolysiloxanes represented by the following formula (7), cyclic organopolysiloxanes represented by the following formula (8) and branched organopolysiloxanes represented by the following formula (9).

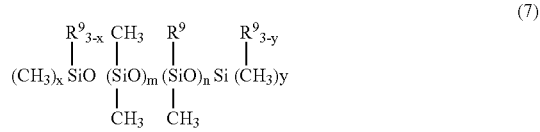

The present cosmetic may further comprise at least one selected from the group consisting of (b) an unctuous agent, (c) a compound having an alcoholic hydroxyl group, (d) water, (e) powder and/or a pigment, and (f) a surfactant The present cosmetic may be skin care cosmetic, hair cosmetic, antiperspirant, makeup cosmetic, or UV-ray protective cosmetic in the form of liquid, milky lotion, cream, solid, paste, gel, multilayer, mousse, spray or stick.

Another aspect of the present invention is a composition comprising the organopolysiloxane wax represented by the formula (1) and a silicone unctuous agent which is liquid at 25° C. in a weight ratio of from 1:0.01 to 1:45.

DESCRIPTION OF THE PREFERRED EMBODIMENTS

The present cosmetic comprises the organopolysiloxane wax represented by the following formula (1).

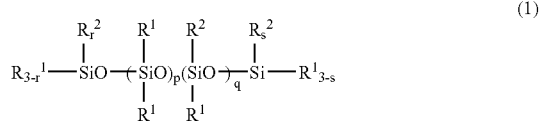
(1)

In the formula (1), $R^1$ is a group selected from the group consisting of alkyl groups having 1 to 20 carbon atoms, alicyclic groups, aryl groups, aralkyl groups and fluorinated alkyl groups;

$R^2$ is a group having a pentaerythritol higher fatty acid polyester residue represented by the following formula (2), $$(CH_2OCOR^8)_m(CH_2O\text{—}X\text{—})_{4-m} \quad (2)$$

wherein $1 \leq m < 4$ or a group having a dipentaerythritol higher fatty acid polyester residue represented by the following formula (3), $$O(CH_2C)_2(CH_2OCO\,R^8)_n(CH_2O\text{—}X\text{—})_{6-n} \quad (3)$$

wherein $1 \leq n < 6$;

$R^8$ in the formulae (2) and (3) being a linear, saturated or unsaturated, aliphatic group having 17 to 30 carbon atoms;

—X— in the formulae (2) and (3) is anyone of the following moieties,

,

, wherein $R^3$ is a $C_3$-$C_8$ alkylene group or a cycloalkylene group, $R^4$ is a $C_4$-$C_{20}$ aliphatic or alicyclic group having at least one group selected from the group consisting of carboxyl, carbonyloxy and hydroxyl groups, p, q, r and s each is a number with $0 \leq p \leq 200$, $0 \leq q \leq 200$, $0 \leq r \leq 3$, and $0 \leq s \leq 3$, provided that $0 \leq p+q \leq 200$ and $1 \leq q+r+s$.

Examples for $R^1$ include alkyl groups such as methyl, ethyl, propyl, butyl, pentyl, hexyl, heptyl, octyl, nonyl and decyl groups; alicyclic groups such as cyclopentyl and cyclohexyl groups; aryl groups such as phenyl and tolyl groups; aralkyl groups such as benzyl and phenetyl groups; fluorinated alkyl groups such as trifluoropropyl and heptadecafluorodecyl groups, among which methyl, phenyl and trifluoropropyl groups are preferred.

As the higher fatty acid $R^8COOH$, use is made of a saturated or unsaturated fatty acid having 18 to 31, preferably 18 to 26 carbon atoms. Examples of the higher fatty acid include stearic acid, nonadecanoic acid, arachic acid, behenic acid, lignoceric acid, cerotic acid, heptacosanic acid, montanic acid, linolic acid, linoleic acid, and arachidonic acid, among which preferred are behenic acid and stearic acid. More preferred is behenic acid, particularly behenic acid having a purity of 90% or higher, and most preferred is behenic acid having a purity of 95% or higher.

In the formulae (2) and (3), the (di)pentaerythritol higher fatty acid polyester residue is derived from a (di)pentaerythritol higher fatty acid polyester (hereinafter referred to as higher fatty acid ester). The higher fatty acid ester can be prepared by esterification between a higher fatty acid and pentaerythritol or dipentaerythritol. The esterification can be performed by any known method. For example, pentaerythritol reacts with behenic acid having 22 carbon atoms as follows:

$$C(CH_2OH)_4 + mC_{21}H_{43}COOH \rightarrow (CH_2OH)_{4-m}C(CH_2OCOC_{21}H_{43})_m \quad (4)$$

wherein m is an integer of from 1 to 4.

Dipentaerythritol reacts with behenic acid as follows:

$$O(CH_2C)_2(CH_2OH)_6 + nC_{21}H_{43}COOH \rightarrow O(CH_2C)_2(CH_2OH)_{6-n}(CH_2OCOC_{21}H_{43})_n \quad (5)$$

wherein n is an integer of from 1 to 6.

In the higher fatty acid ester residue, m is a number of from 1 to 3, preferably 2 or 3, and n is a number of from 1 to 5, preferably from 3 to 5. Thus, the term, "poly", as used herein, includes "mono." A higher fatty acid polyester with m=4 or n=6 having no hydroxyl group in the molecule is not preferred because such a fatty acid ester cannot bond to an organopolysiloxane and remains unreacted. This requires an undesirable purification process to remove the remaining fatty acid ester by, for example, fractionation according to molecular weights. A fatty acid ester having two or more of hydroxyl groups is reacted preferably with an organbpolysiloxane having one reactive group to prevent gellation. As mentioned above, m and n each can be two or more different numbers. Practically, an average of m or n is determined and reaction conditions are set depending on the average.

The pentaerythritol higher fatty acid ester having the aforesaid preferred range of m can be obtained by reacting 1 mole of pentaerythritol with about 3 or fewer moles of a higher fatty acid. A mixture of pentaerythritol higher fatty acid tetraester, pentaerythritol higher fatty acid triester and pentaerythritol higher fatty acid diester can be obtained.

The dipentaerythritol higher fatty acid ester having the aforesaid preferred range of n can be obtained by reacting 1 mole of dipentaerythritol with about 5 or fewer moles of a higher fatty acid. A mixture of dipentaerythritol higher fatty acid hexaexter, dipentaerythritol higher fatty acid pentaester, dipentaerythritol higher fatty acid tetraester and dipentaerythritol higher fatty acid triester can be obtained.

The aforesaid (di) pentaerythritol higher fatty acid ester residue is bonded to an Si atom of an organopolysiloxane via any one of the following moieties,

wherein $R^3$ is a $C_3$-$C_8$, preferably $C_3$-$C_6$ alkylene group or alicyclic group. $R^4$ is a $C_4$-$C_{20}$, preferably $C_6$-$C_8$ aliphatic or alicyclic hydrocarbon group having at least one selected from the group consisting of carboxyl, carbonyloxy and hydroxyl groups. The preferred $R^4$ include the following moieties,

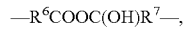

wherein $R^5$ is a $C_3$-$C_8$ alkylene or a cycloalkylene group, $R^6$ is a $C_3$-$C_8$ alkylene group, and $R^7$ is a $C_3$-$C_8$ alkylene or cycloalkylene group.

The wax with X being —$R_3$— can be prepared by the following two methods.

The first method comprises the steps of reacting (di) pentaerythritol higher fatty acid polyester with an organic chloride having a double bond at an end to prepare (di)pentaerythritol higher fatty acid polyester allyl ether, and then reacting the double bond of the ether with an organohydrogenpolysiloxane in the presence of a platinum catalyst.

For example, pentaerythritol polybehenate reacts with allyl chloride as follows:

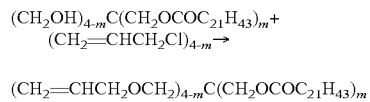

The second method comprises the steps of synthesizing a (di)pentaerythritol monoallyl ether having a double bond at an end as follows,

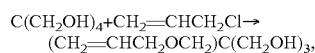

preparing a higher fatty acid polyester allyl ether by reacting the remaining hydroxyl group in the above allyl ether with a higher fatty acid, and reacting the ether with an organohydrogenpolysiloxane in the presence of a platinum catalyst.

The organohydrogenpolysiloxane may have an —SiH functional group either at an end or at any other location in the molecule, and is preferably represented by the following general formula (6),

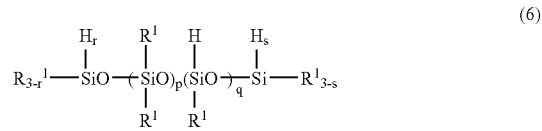

wherein $R^1$, p, q, r, and s are as defined above concerning the formula (1).

The reaction of the organohydrogenpolysiloxane with (di) pentaerythritol higher fatty acid polyester having a double bond at an end may be performed in any known manner in the presence of a platinum catalyst in a solvent or without a solvent. A reaction temperature may range from 30 to 150° C., preferably from 60° C. to 120° C.

A molar ratio of the terminal double bond to the —SiH group in the organohydrogenpolysiloxane, double bond/SiH, is not limited, but preferably in the range of from 1.05 to 1.2.

The wax with X being —CO R$_4$— can be prepared by the following two methods.

The first method is to react (di)pentaerythritol higher fatty acid polyester with an organopolysiloxane modified with an acid anhydride. The acid anhydride-modified organopolysiloxane can be prepared by a known method, for example, by addition-reacting an acid anhydride having an unsaturated group such as allyl succinic anhydride and 5-norbornene-2,3-dicarboxylic anhydride with an organohydrogenpolysiloxane, preferably the one represented by the above formula (6), in the presence of a platinum catalyst.

The following structure, for instance, is obtained from pentaerythritol polybehenate and allyl succinic anhydride

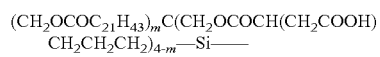
(CH$_2$OCOC$_{21}$H$_{43}$)$_m$C(CH$_2$OCOCH(CH$_2$COOH)
CH$_2$CH$_2$CH$_2$)$_{4-m}$—Si—— wherein —Si—— represents a polysiloxane moiety.

A molar ratio of the acid anhydride bond of the acid anhydride-modified organopolysiloxane to the hydroxyl group of (di)pentaerythritol higher fatty acid polyester, i.e., acid anhydride bond moiety/hydroxyl group, is preferably in the range of from 0.8 to 1.2.

The second method to prepare the wax with X being —CO R$_4$— comprises the steps of reacting a remaining hydroxyl group of (di)pentaerythritol higher fatty acid polyester with at least an equimolar amount of a cyclic acid anhydride to introduce a carboxyl group, reacting the carboxyl group with an excess molar amount of an epoxy compound having a double bond, and isolating the obtained alkenylated (di)pentaerythritol higher fatty acid polyester which then is reacted with an organohydrogenpolysiloxane preferably represented by the above-mentioned formula (6) in the presence of a platinum catalyst.

Any cyclic acid anhydride may be used, but preferably succinic anhydride is used. As the epoxy compound having a double bond, allyl glycidyl ether, and vinyl cyclohexene oxide are preferably used. The organohydrogenpolysiloxane may have an -SiH functional group either at an end or at any other location in the molecule, and is preferably represented by the above-mentioned formula (6). The reaction between the organohydrogenpolysiloxane and (di)pentaerythritol higher fatty acid polyester having a terminal double bond is described above.

The following structure is obtained from, for instance, pentaerythritol polybehenate, succinic anhydride, allyl glycidyl ether and organohydrogenpolysiloxane

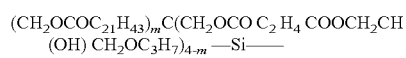
(CH$_2$OCOC$_{21}$H$_{43}$)$_m$C(CH$_2$OCO C$_2$H$_4$ COOCH$_2$CH
(OH) CH$_2$OC$_3$H$_7$)$_{4-m}$—Si—— wherein —Si—— represents a polysiloxane moiety.

In any of the aforesaid reactions, a solvent may or may not be used. Preferably, a solvent is used to improve compatibility between organohydrogenpolysiloxane or organopolysiloxane modified with acid anhydride and higher fatty acid ester. A reaction temperature is preferably 80° C. or higher, particularly 100° C. or higher to perform the reaction at a temperature higher than a melting point of a higher fatty acid ester. A catalyst may or may not be used in the reaction between the acid anhydride-modified silicone and (di) pentaerythritol higher fatty acid ester. When it is used, metal soaps, alkaline metal salts of organic acids are preferably used.

In the reaction between an organohydrogenpolysiloxane and (di)pentaerythritol higher fatty acid ester, noble metal catalysts, particularly catalyst derived from chloroplatinic acid are used.

The organopolysiloxane modified with a higher fatty acid ester thus obtained has an endothermic peak as measured with a differential scanning calorimeter, DSC, in a heating rate of 10° C./min, which peak has an apex at a temperature of 60° C. or higher, preferably 70° C. or higher. The melting point is higher than those of around 50° C. of known silicones modified with a higher fatty acid ester. When mixed with a liquid unctuous agent, the present organopolysiloxane forms gel or solid which spreads smoothly and can be used for making a cosmetic preparation in the form of liquid, emulsion, paste, or solid.

Preferably, the present organopolysiloxane wax has a weight average molecular weight, reduced to polystyrene, measured by GPC, of from 1,000 to 8,000, more preferably from 2,000 to 7,000, most preferably from 3,000 to 6,000.

The present organopolysiloxane wax modified with higher fatty acid ester can be used for various kinds of cosmetics. It is particularly suitable raw material for external cosmetics applied to the skin or the hair such as skin care products, makeup products, hair care products, antiperspirant products, UV-ray protective products.

In the cosmetic, a content of the organopolysiloxane modified with fatty acid ester can range from 0.5 to 95 wt %, preferably from 1 to 70 wt %, according to a type of (a) a silicone oil contained in the cosmetic, based on a total weight of the cosmetic. In a cream form cosmetic, for instance, the content may range from 0.5 to 10 wt %, preferably from 0.5 to 5 wt % based on a total weight of the cosmetic. In a solid or stick-shaped cosmetic containing powdery components in an amount of 25% or lower, the content may range from 5 to 70 wt %, preferably from 2 to 50 wt % based on a total weight of the cosmetic preparation. In a solid cosmetic containing powdery components in an amount of 80% or higher, the content may range form 1 to 10 wt %, preferably from 1 to 5 wt % based on a total weight of the cosmetic.

The organopolysiloxane wax modified with higher fatty acid ester is preferably incorporated in a cosmetic together with (a) a silicone oil. The silicone oil (a) as used herein include not only silicone compounds which are liquid at 25° C., but also silicones which are resinous or gummy at 25 ° C. dissolved or dispersed in a silicone having a low viscosity, such as conventionally used silicone oil, hydrocarbon oil, or ester oil. These silicon oils, by mixing with the aforesaid organopolysiloxane wax modified with higher fatty acid ester, give a lubricious pasty or solid composition which spread smoothly.

Preferred examples of the silicone oil include the following silicone oils.

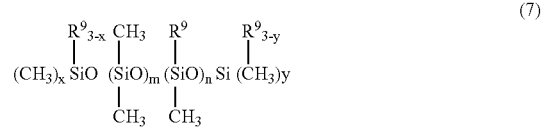

(7)

(8)

(CH$_3$)$_{4-r}$Si{OSi(CH$_3$)$_3$}$_r$       (9)

In the above formulas, R$^9$ is selected from the group consisting of a hydrogen atom, a hydroxyl group, unsubstituted or fluorinated alkyl groups having 1 to 20 carbon atoms, aryl groups, amino-substituted alkyl groups, alkoxy groups and a group represented by the formula, (CH$_3$)$_3$SiO{(CH$_3$)$_2$SiO}$_s$Si(CH$_3$)$_2$CH$_2$CH$_2$—; m is an integer of from 0 to 1000, n is an integer of from 0 to 1000, with m+n ranging from 1 to 1000; x and y each is 0, 1, 2 or 3; p and q each is an integer of from 0 to 8 with $3 \leqq p+q \leqq 8$; r is an integer of from 1 to 4; and s is an integer of from 0 to 500.

Examples of $R^9$ include methyl, ethyl, propyl, butyl, hexyl, octyl, decyl, dodecyl, tetradecyl, hexadecyl, octadecyl, trifluoropropyl, nonafluorohexyl, heptadecylfluorodecyl, phenyl, aminopropyl, dimethylaminopropyl, aminoethylaminopropyl, stearoxy, butoxy, ethoxy, propoxy, cetyloxy, myristyloxy, styryl, and α-methylstyryl groups, hexyl, octyl, decyl, dodecyl, tetradecyl, hexadecyl, octadecyl, trifluoropropyl, phenyl, aminopropyl, and aminoethylaminopropyl groups.

Examples of the silicone oil (a) of the above formula include organopolysiloxanes which are liquid at room temperature having a low viscosity to a high viscosity, preferably from 0.65 to 1,000,000 mm²/s, such as dimethylpolysiloxane, methylphenylpolysiloxane, methylhydrogenpolysiloxane, dimethylsiloxane/methyphenylsiloxane copolymer; cyclic siloxanes such as octamethylcyclotetrasiloxane (D4), decamethylcyclopentasiloxane (D5), dodecamethylcyclohexasiloxane (D6), tetramethyltetrahydrogencyclotetrasiloxane (H4), and tetramethyltetraphenylcycloterasiloxane; branched siloxanes such as tristrimethylsiloxysilane (M3T), tetrakistrimethylsiloxysilane (M4Q), tristrimethylsiloxyphenylsilane; higher alkoxy-modified silicones such as stearoxy silicone; alkyl-modified silicones; amino-modified silicones; and fluorine-modified silicones.

One of the preferred silicone resins used in dissolved or dispersed state in a low viscosity oil is a crosslinked organopolysiloxane swollen with a silicone oil having a viscosity of from 0.65 to 10.0 mm²/s in an amount larger than or equal to the weight of the crosslinked organopolysiloxane itself, which crosslinked organopolysiloxane is prepared by reacting an alkylhydrogenpolysiloxane with a crosslinker having at least two reactive vinyl groups in a molecule.

Examples of the alkylhydrogenpolysiloxane include linear or branched methylhydrogenpolysiloxanes, methylhydrogenpolysiloxanes grafted with an alkyl chain having 6 to 20 carbon atoms, and methylhydrogenpolysiloxanes grafted with a polyoxyethylene chain. The number of SiH group per molecule should be two or more on the average.

Examples of the crosslinker include compounds having two or more of vinyl groups such as methylvinylpolysiloxane, α, ω-alkenyldiene, glycerin triallyl ether, polyoxyalkyneylated glycerin triallyl ether, trimethylolpropane triallyl ether, and polyoxyalkynylated trimethylolpropane triallyl ether.

The crosslinked organopolysiloxane preferably has at least one moiety selected from the group consisting of polyoxyalkylene, polyglycerin, alkyl, alkenyl, aryl, and fluoroalkyl moieties in a molecule. Preferred examples of the crosslinked organopolysiloxane are described in Japanese Patent Application Laid-Open No. H2-43263, Japanese Patent Application Laid-Open No. H2-214775, Japanese Patent No. 2631772, Japanese Patent Application Laid-Open No. H9-136813(KSG30), Japanese Patent Application Laid-Open No. 2001-342255, WO 03/20828(KSG210), and WO 03/24413(KSG40). The crosslinked organopolysiloxane can give a non-shiny and mat finish, improve affinity to the skin and prevent color migration.

Examples of the composition comprising the crosslinked organopolysiloxane and the oil agent such as silicone oil, hydrocarbon oil, or ester oil, include KSG-15, 16, 17, 18, 21, 210, 31, 32, 33, 34, 310, 320, 330, 340, 41, 42, 43, 44, 710, 810, 820, 830 and 840, all available from Shin-Etsu Chemical Co. Ltd.

The second preferred silicone resin used in dissolved or dispersed state in an oil agent having a low viscosity is a silicone resin which is gummy or solid at room temperature and soluble in decamethylcyclopentasiloxane. Preferably, the gummy silicone resin is a linear silicone represented by the formula, $(CH_3)_3SiO\{(CH_3)_2SiO\}_{t\{(CH3)}}R^{10}SiO\}_u Si(CH_3)_3$, wherein $R^{10}$ is selected from the group consisting of alkyl groups having 6 to 20 carbon atoms, amino-substituted alkyl groups having 3 to 15 carbon atoms, fluorinated alkyl groups, alkyl groups having a quarterly ammonium group, t ranges from 1001 to 20000, and u ranges from 0 to 5000 with t+u ranging from 1001 to 25000.

Preferred solid silicone resin is a silicone network compound having a combination of trialkylsiloxy units (i.e., M units), dialkylsiloxy units (i.e., D units), monoalkylsiloxy units (i.e., T units), and tetra functional units (i.e. Q units), for example, MQ resin, MDQ resin, MTQ resin, MDTQ resin, TD resin, TQ resin, and TDQ resin. Preferably, the a silicone network compound has at least one moiety selected from the group consisting of pyrrolidone, long alkyl chains, polyoxyalkylene, and fluoroalkyl moieties in a molecule(Japanese Patent Application Laid-Open No. 2000-234062, and Japanese Patent No. 3218872).

The third preferred silicone resin used in dissolved or dispersed state in an oil agent having a low viscosity is an acrylic silicone resin which is semisolid or solid at room temperature dissolved in a volatile silicone, a volatile hydrocarbon oil, a non-volatile silicone, or a non-volatile hydrocarbon oil. Preferably, the acrylic silicone resin has at least one moiety selected from the group consisting of pyrrolidone, long alkyl chains, polyoxyalkylene, and fluoroalkyl moieties in a molecule. The acrylic silicone resin may be an acrylic/silicone graft or block copolymer (Japanese Patent Application Laid-Open No. H1-319518, Japanese Patent No. 2704730, Japanese Patent No. 2767633, Japanese Patent No. 2767636, and Japanese Patent Application Laid-Open No. 2000-344829).

Among the aforesaid silicone oils, dimethylpolysiloxanes having a viscosity of from 1 to 30 mm²/s at 25° C., decamethylcyclopentasiloxane, the crosslinked dimethylpolysiloxane swollen with a silicone oil having a viscosity of from 0.65 to 10.0 mm2/S in an amount larger than or equal to the weight of the crosslinked organopolysiloxane itself, the crosslinked polyether-modified silicone, and the acrylic silicone resin dissolved in a volatile oil are preferably used. These silicone oils may be used alone or a mixture.

The organopolysiloxane modified with (di)pentaerythritol higher fatty acid ester, represented by the formula (1), and the silicone oil (a) are incorporated in the cosmetic preparation as a homogeneous composition in the form of paste, gel, or solid prepared by mixing the organopolysiloxane with the silicone oil (a) in a weight ratio of from 1:0.01 to 1:45, preferably from 1:0.5 to 1:20. The content of the silicone oil (a) including the content of the solvent oil can be adjusted according to an intended use of the cosmetic and, typically, ranges from 1 to 70 wt %, preferably from 3 to 60 wt %, based on a total weight of the cosmetic.

In addition to the silicone oil (a), the present cosmetic preparation can contain (b) an unctuous agent according to an intended use of the cosmetic. Any unctuous agent commonly used for cosmetics can be used regardless of its form such as solid, semi-solid or liquid. Examples of the unctuous agent (b) include natural animal or plant oils, semi-synthetic oils, hydrocarbon oils, higher alcohols, and ester oils.

Examples of natural animal or plant oils and semi-synthetic oils include avocado oil, linseed oil, almond oil, Ibota wax, perilla oil, olive oil, cacao butter, kapok wax, kaya oil, carnauba wax, Glycyrrhiza oil, candelilla wax, beef tallow, neat's-foot oil, beef bone fat, hydrogenated beef tallow, apricot kernel oil, spermaceti wax, hydrogenated oil, wheat germ oil, sesame oil, rice germ oil, rice bran oil, sugar cane wax, sasanqua oil, safflower oil, shear butter, Chinese tung oil, cinnamon oil, jojoba wax, shellac wax, turtle oil, soybean oil, tea seed oil, camellia oil, evening primrose oil, corn oil, lard, rapeseed oil, Japanese tung oil, rice bran oil, germ oil, horse fat, persic oil, palm oil, palm kernel oil, castor oil, hydrogenated castor oil, castor oil fatty acid methylester, sunflower oil, grape oil, bayberry wax, jojoba oil, macadamia nut oil, beeswax, mink oil, cottonseed oil, cotton wax, Japanese wax, Japanese wax kernel oil, montan wax, coconut oil, hydrogenated coconut oil, tri-coconut oil fatty acid glyceride, mutton tallow, peanut oil, lanolin, liquid lanolin, hydrogenated lanolin, lanolin alcohol, hard lanolin, lanolin acetate, isopropyl lanolate, hexyl laurate, POE lanolin alcohol ether, POE lanolin alcohol acetate, polyethylene glycol lanolate, POE hydrogenated lanolin alcohol ether, and egg yolk oil, wherein POE stands for polyoxyethylene.

Examples of the hydrocarbon oils include ozokerite, squalane, squalene, ceresin, paraffin, paraffin wax, liquid paraffin, pristane, polyisobutylene, microcrystalline wax, and Vaseline; higher fatty acids, e.g., lauric acid, myristic acid, palmitic acid, stearic acid, behenic acid, undecylenic acid, oleic acid, linoleic acid, linolenic acid, arachidonic acid, eicosapentaenoic acid (EPA), docosahexaenoic acid (DHA), isostearic acid, and 12-hydroxystearic acid. Examples of higher alcohols include lauryl alcohol, myristyl alcohol, palmityl alcohol, stearyl alcohol, behenyl alcohol, hexadecyl alcohol, oleyl alcohol, isostearyl alcohol, hexyldodecanol, octyl dodecanol, cetostearyl alcohol, 2-decyltetradecinol, cholesterol, phytosterol, POE cholesterol ether, monostearyl glycerin ether (batyl alcohol), and monooleyl glyceryl ether (cerakyl alcohol).

Examples of the ester oils include diisobutyl adipate, 2-hexyldecyl adipate, di-2-heptylundecyladipate, N-alkyl glycolmonoisostearate, isocetyl isostearate, trimethylolpropane triisostearate, ethylene glycol di-2-ethylhexanoate, cetyl 2-ethylhexanoate, trimethylolpropane tri-2-ethylhexanoate, pentaerythritol tetra-2-ethylhexanoate, cetyl octanoate, octyldodecyl gum ester, oleyl oleate, octyldodecyl oleate, decyl oleate, isononyl isononanate, neopentyl glycol dicaprirate, triethyl citrate, 2-ethylhexyl succinate, amyl acetate, ethyl acetate, butyl acetate, isocetyl stearate, butyl stearate, diisopropyl sebacinate, di-2-ethylhexyl sebacinate, cetyl lactate, myristyl lactate, isopropyl palmitate, 2-ethylhexyl palmitate, 2-hexyldecyl palmitate, 2-heptylundecyl palmitate, cholesteryl 12-hydroxystearate, dipentaerythritol fatty acid esters, isopropyl myristate, octyldodecyl myristate, 2-hexyldecyl myristate, myristyl myristate, hexyldecyl dimethyloctanoate, ethyl laurate, hexyl laurate, 2-octyldodecyl N-lauroyl-L-glutamate, and diisostearyl malate; and glyceride oils, e.g., acetoglyceryl, glycerol triisooctanoate, glyceryl triisostearate, glyceryl triisopalmitate, glyceryl monostearate, glyceryl di-2-heptylundecanoate, glyceryl trimyristate, and diglyceryl myristyl isostearate.

Examples of fluorinated oils include perfluoropolyether, perfluorodecarine, and perfluorooctane.

These unctuous agent (b) is incorporated in the cosmetic preferably in an amount of from 5 to 95 wt % based on a total weight of the cosmetic. In the cosmetic in the form of solid or stick, the unctuous agent is incorporated preferably in an amount of from 10 to 50 wt % based on a total weight of the cosmetic.

The present cosmetic preparation may contain one or more of (c) a compound having an alcoholic hydroxyl group according to an intended use of the cosmetic. Examples of the compound having an alcoholic hydroxyl group include lower alcohols such as ethanol and isopropanol; sugar alcohols such as sorbitol, and maltose; sterols such as cholesterol, sitosterol, phytosterol, and lanosterol; polyhydric alcohols such as butylene glycol, propylene glycol, dibutylene glycol, and pentylene glycol. The compound having an alcoholic hydroxyl group (c) is incorporated in the cosmetic preparation preferably in an amount of from 0.1 to 98 wt % based on a total weight of the cosmetic.

The present cosmetic preparation may contain (d) water according to an intended use of the cosmetic. Water is incorporated in the cosmetic preparation preferably in an amount of from 1 to 95wt % based on a total weight of the cosmetic.

The present cosmetic preparation can contain one or more of (e) powder and/or a pigment according to an intended use of the cosmetic. As the powder, any powder commonly used in cosmetics may be used, regardless of the shape (spherical, rod-like, acicular, tubular, irregular, scaly or spindle forms), particle size (size of fume, fine particles or pigment grade), and particle structure (porous and non-porous). Examples of the powder include inorganic powder, organic powder, powder of surface active agent metal salt, colored pigments, pearl pigments, metallic powder pigments, and natural colors.

Examples of the inorganic powder include titanium oxide, zirconium oxide, zinc oxide, cerium oxide, magnesium oxide, barium sulfate, calcium sulfate, magnesium sulfate, calcium carbonate, magnesium carbonate, talc, mica, kaolin, cericite, muscovite, synthetic mica, phlogopite, lepidolite, biotite, lithia mica, silicic acid, silicic anhydride, aluminum silicate, magnesium silicate, aluminum magnesium silicate, calcium silicate, barium silicate, strontium silicate, metal salts of tungstenic acid, hydroxyapatite, vermiculite, higilite, bentonite, montmorillonite, hectolitre, zeolite, ceramics powder, dibasic calcium phosphate, alumina, aluminum hydroxide, boron nitride, and silica.

Examples of the organic powder include polyamide powder, polyester powder, polyethylene powder, polypropylene powder, polystyrene powder, polyurethane powder, benzoguanamine powder, polymethylbenzoguanamine powder, polytetrafluoroethylene powder, polymethylmethacrylate powder, cellulose powder, silk powder, nylon powder such as Nylon 12 and Nylon 6, crosslinked dimethylsilicone fine powder, polymethylsilsesquioxane fine powder, composite fine powder of spherical silicone rubber coated with polymethylsilsesquioxane fine particles, styrene/acrylic acid copolymer, divinylbenzene/styrene copolymer, vinyl resin, urea resin, phenol resin, fluororesin, silicone resin, acrylic resin, melamine resin, epoxy resin, polycarbonate resin, microcrystalline fiber powder, starch powder, and lauroyl lysine.

Examples of the surface active agent metal salt powder include zinc stearate, aluminum stearate, calcium stearate, magnesium stearate, zinc myristate, magnesium myristate, zinc cetyl phosphate, calcium cetyl phosphate, and zinc/sodium cetyl phosphate.

Examples of colored pigments include inorganic red pigments such as iron oxide, iron hydroxide, and iron titanate; inorganic brown pigments such as γ-iron oxide; inorganic yellow pigments such as iron oxide yellow and loess; inorganic black pigments such as iron oxide black and carbon black; inorganic violet pigments such as manganese violet and cobalt violet; inorganic green pigments such as chromium hydroxide, chromium oxide, cobalt oxide, and cobalt titanate; inorganic blue pigments such as Prussian blue and ultramarine blue; lakes of tar pigments, lakes of natural dyes, and synthetic resin powder complexes thereof.

Examples of the pearl pigments include titanium oxide-coated mica, bismuth oxychloride, titanium oxide-coated bismuth oxychloride, titanium oxide-coated talc, fish scales, and titanium oxide-coated colored mica. Examples of metal powder include aluminum powder, copper powder, and stainless steel powder.

Examples of the tar pigments include Red No. 3, Red No. 104, Red No. 106, Red No. 201, Red No. 202, Red No. 204, Red No. 205, Red No. 220, Red No. 226, Red No. 227, Red No. 228, Red No. 230, Red No. 401, Red No. 505, Yellow No. 4, Yellow No. 5, Yellow No. 202, Yellow No. 203, Yellow No. 204, Yellow No. 401, Blue No. 1, Blue No. 2, Blue No. 201, Blue No. 404, Green No. 3, Green No. 201, Green No. 204, Green No. 205, Orange No. 201, Orange No. 203, Orange No. 204, Orange No. 206, and Orange No. 207. Examples of the natural pigments include carminic acid, laccaic acid, carthamin, brazilin, and crocin.

These powder may be used in the form of a composite, or a mixture of two or more or the powder, or may be surface-treated with a oil for general use, silicone oils, a fluorine compound, or surfactant, as far as the object of the present invention is not adversely affected. The powder is incorporated in the cosmetic preferably in an amount of from 0.1 to 99 wt % based on a total weight of the cosmetic preparation. In a solid powder cosmetic, it is contained preferably in an amount of from 80 to 99 wt % based on a total weight of the cosmetic preparation.

The present cosmetic preparation may contain one or more of (f) a surfactant according to an intended use of the cosmetic. Any surfactant commonly used for a cosmetic can be used, for example, anionic, cationic, nonionic, and amphoteric surfactant.

Examples of the anionic surfactant include fatty acid soaps, such as sodium stearate and triethanolamine palmitate, alkylether carboxylic acids and salts thereof, carboxylates of condensates from amino acids and fatty acids, alkyl sulfonic acids, alkenesulfonates, fatty acid ester sulfonates, fatty acid amide sulfonates, sulfonate salts of the formalin condensates with alkyl sulfonates, salts of sulfate esters such as salts of alkyl sulfates, salts of secondary higher alcohol sulfates, salts of alkyl/allyl ether sulfates, salts of fatty acid ester sulfates, salts of fatty acid alkylolamide sulfates, and Turkey Red oil, alkyl phosphates, ether phosphates, alkylallylether phosphates, amide phosphates, and N-acylamino surfactants. Examples of the cationic surfactants including amine salts such as alkylamine salts, polyamine and amino alcohol fatty acid derivatives, alkyl quaternary ammonium salts, aromatic quaternary ammonium salts, pyridium salts and imidazolium salts.

Examples of the nonionic surfactant include sorbitan fatty acid esters, glycerin fatty acid esters, polyglycerin fatty acid esters, propylene glycol fatty acid esters, polyethylene glycol fatty acid esters, sucrose fatty acid esters, polyoxyethylene alkylethers, polyoxypropylene alkylethers, polyoxyethylene alkylphenylether, polyoxyethylene fatty acid esters, polyoxyethylene sorbitan fatty acid esters, polyoxyethylene sorbitol fatty acid esters, polyoxyethylene glycerin fatty acid esters, polyoxyethylene propylene glycol fatty acid esters, polyoxyethylene castor oil, polyoxyethylene hydrogenated castor oil, polyoxyethylene phytostanolether, polyoxyethylene phytosterolether, polyoxyethylene cholestanolether, polyoxyethylene cholesterylether, polyoxyalkylene-modified organopolysiloxane(Japanese Patent No. 2137062, Japanese Patent Application Laid-Open No. H7-330907), polyglycerin-modified organopolysiloxane(Japanese Patent Publication No. S62-34039, Japanese Patent No. 2613124, Japanese Patent No. 2844453, Japanese Patent Application Laid-Open No. 2002-179798), polyalkylene- and alkyl-modified organopolysiloxane (Japanese Patent Application Laid-Open No. 61-90732, Japanese Patent Application Laid-Open No. H9-59386) alkanolamide, sugar ethers, or sugar amides.

Examples of the amphoteric surfactant include betaine, aminocarboxylic acid salt, imidazoline derivatives and amideamine type. The surfactant is incorporated in the cosmetic preparation preferably in an amount of from 0.1 to 20 wt %, particularly from 0.2 to 10 wt % based on a total weight of the cosmetic.

In the cosmetic of the present invention, a variety of components that are commonly used in cosmetics can be blended in addition to the aforementioned components, as far as the purpose of the present invention is not damaged, for example, oil-soluble gelling agents, clay minerals modified with organic compounds, resins, antiperspirants, UV-ray absorbents, UV-ray absorbing and scattering agents, moisture retention agents, antiseptics, anti-microbial agents, perfumes, salts, antioxidants, pH regulators, a chelating agents, refreshing agents, an anti-inflammatory agent, skin beautifying components, such as skin whitener, cell activator, rough dry skin improver, blood circulation promoter, skin astringent and anti-seborrheic agent, vitamins, amino acids, nucleic acids, hormones, clathrate compounds, and hair setting agents.

Examples of oil-soluble gelling agents include aluminum stearate, magnesium stearate, and zinc myristate; a amino acid derivatives such as N-lauroyl-L-glutamic acid, $\alpha$, $\gamma$-di-n-butylamine; dextrin fatty acid esters such as dextrin palmitate, dextrin stearate, and dextrin 2-ethylhexane palmitate; sucrose fatty acid esters such as sucrose palmitate and sucrose stearate; benzylidene derivatives of sorbitol such as monobenzylidene sorbitol and dibenzylidene sorbitol; clay minerals modified with an organic moiety such as dimethylbenzyldodecylammonium montmorillonite clay, dimethyldioctadecylammonium montmorillonite, and octadecyldimethylbenzylammonium montmorillonite.

Examples of the antiperspirant include aluminum chlorohydrate, aluminum chloride, aluminum sesquichlorohydrate, zirconium hydoxychloride, aluminum zirconium hydroxychloride, and aluminum zirconium glycine complex.

Examples of the UV-ray absorbents include UV-ray absorbents of benzoic acid type, such as p-aminobenzoic acid; those of anthranilic acid type, such as methyl anthranilate; those of salicylic acid type, such as methyl salicylate; those of succinic acid type, such as octyl p-methoxysuccinate; those of benzophenone type, such as 2,4-dihydroxybenzophenone; those of urocanic acid type, such as ethyl urocanate; and those of dibenzoylmethane type, such as 4-t-butyl-4'-methoxydibenzoylmethane. Examples of the UV-ray absorbing and scattering agents include fine powder of titanium oxide, fine powder of iron-containing titanium oxide, fine powder of zinc oxide, fine powder of cerium oxide, and a mixture thereof.

Examples of a moisture retention agent include glycerin, sorbitol, propylene glycol, dipropylene glycol, 1,3-butylene glycol, pentylene glycol, glucose, xylitol, maltitol, polyethylene glycol, hyaluronic acid, chondroitin sulfuric acid, pyrrolidone carboxylate, polyoxyethylene glycoside, and polyoxypropylene methylglycoside.

Examples of antiseptics include alkyl paraoxybenzoates, benzoic acid, sodium benzoate, sorbic acid, potassium sorbate, and phenoxyethanol may be used. For the antibacterial agents, benzoic acid, salicylic acid, carbolic acid, sorbic acid, paraoxybenzoic acid alkyl esters, parachlorometracresol, hexachlorophene, benzalkonium chloride, chlorohexydine chloride, trichlorocarbanilide, triclosan, photosensitizer and phenoxyethanol.

Examples of the antioxidants include tocopherol, butylhydroxyanisole, dibutylhydroxytoluene, and phytin. Examples of the pH regulator include lactic acid, citric acid, glycolic acid, succinic acid, oxalic acid, dl-malic acid, calcium carbonate, sodium hydrogen carbonate, and ammonium hydrogen carbonate. Examples of the chelating agent include alanine, sodium edetate, sodium polyphosphate, sodium methaphosphate, and phosphoric acid. Examples of the cooling agents include l-menthol and camphor. Examples of the anti-inflammatory agents include arantoin, glycyrrhizic acid and salts thereof, glycyrrhetic acid and stearyl glycyrrhetate, tranexamic acid, and azulene.

Examples of the skin-beautifying components include whitening agents, such as placenta extract, arbutin, glutathione and Yukinoshita extract; cell activators, such as royal jelly, photosensitizers, cholesterol derivatives and calf blood extract; rough and dry skin improvers; blood circulation improvers, such as nonylic acid vanillyl amide, benzyl nicotinate, beta-butoxyethyl nicotinate, capsaicin, zingerone, cantharis tincture, ichtammol, caffeine, tannic acid, alpha-borneol, tocopheryl nicotinate, inositol hexanicotinate, cyclandelate, cinnarizine, tolazoline, acetyl choline, verapamil, cepharanthin and gamma-oryzanol; skin astringents, such as zinc oxide and tannic acid; and anti-seborrheic agents, such as sulfur and thianthol.

Examples of the vitamins include vitamin A, such as vitamin A oil, retinol, retinyl acetate and retinyl palmitate; vitamin B, including vitamin $B_2$ such as riboflavin, riboflavin butyrate and flavin adenine nucleotide, vitamin $B_6$ such as pyridoxine hydrochloride, pyridoxine dioctanoate and pyridoxine tripalmitate, vitamin $B_{12}$ and its derivatives, and vitamin B15 and its derivatives; vitamin C, such as L-ascorbic acid, L-ascorbic acid dipalmitic ester, sodium (L-ascorbic acid)-2-sulfate and dipotassium L-ascorbic acid diphosphate; vitamin D, such as ergocalciferol and cholecarciferol; vitamin E, such as alpha-tocopherol, beta-tocopherol, gamma-tocopherol, dl-alpha-tocopheryl acetate, dl-alpha-tocopheryl nicotinate and dl-alpha-tocopheryl succinate; vitamin H; vitamin P; nicotinic acids, such as nicotinic acid, benzyl nicotinate and nicotinic acid amide; pantothenic acids, such as calcium pantothenate, D-pantothenyl alcohol, pantothenyl ethyl ether and acetylpantothenyl ethyl ether; and biotin.

Examples of the amino acids include glycine, valine, leucine, isoleucine, serine, threonine, phenylaranine, alginine, lysine, aspartic acid, glutamic acid, cystine, cysteine, methionine, and tryptophan; examples of the nucleic acids include deoxyribonucleic acid; and examples of the hormones include estradiol and ethenyl estradiol.

Examples of the polymers for hair setting include amphoteric, anionic, cationic, and nonionic polymers, such as polymers of polyvinyl pyrrolidone type such as polyvinyl pyrrolidone, vinyl pyrrolidone/vinyl acetate copolymers; acidic polymers of vinyl acetate ether type such as methyl vinyl ether/maleic acid anhydride alkyl half ester copolymer; polymers of acidic poly vinyl acetate type such as vinyl acetate/crotonic acid copolymer; acidic acrylic polymers such as (meth)acrylic acid/alkyl (meth) acrylate copolymer, (meth) acrylic acid/alkyl (meth) acrylate/alkyl acrylic amide copolymer, and amphoteric acrylic polymer such as N-methacryloylethyl-N,N-dimethylammonium alpha-N-methylcarboxybetaine/alkylmetahcrylate copolymer, hydroxypropyl (metha) acrylate/butylaminoethyl methacrylate/octyl amide of acrylic acid copolymer. Use is also made of naturally occurring polymers such as cellulose or derivatives thereof, keratin, collagen and derivatives thereof.

The term "cosmetic" or "cosmetic preparation" as used herein are intended to include skin care products, such as face lotion, milky lotion, cream, face cleansing cream, massage materials, toilet soap and detergent, antiperspirant and deodorant; makeup products, such as face powder, foundation, rouge, eye shadow, mascara, eyeliner and lipstick; and hairdressing products, such as shampoo, rinse, treatment setting agent, antiperspirant and UV-ray protective cosmetics, such as sunscreen milky lotion or sunscreen cream.

Additionally, the present cosmetic preparation may be in the form of liquid, emulsion, solid, paste, gel, powder, press, laminate, mousse, spray, stick, or pencil forms.

EXAMPLES

The present invention will be explained with reference to the Examples, but not limited thereto. In the description below, "E" represents "wt %" unless otherwise specified.

Preparation Example 1

Pentaerythritol polybehenate (I) was prepared by esterification of pentaerythritol with behenic acid, $$(CH_2OH)_{4-m}C(CH_2OCOC_{21}H_{43})_m \qquad (I)$$

wherein m was a mixture of 2, 3 and 4.

Pentaerythritol polybehenate (I) had an OH value of 54.2 and was a mixture of pentaerythritol tetrabehenate, pentaerythritol tribehenate, and pentaerythritol dibehenate, whereas pure pentaerythritol tribehenate has an OH value of 50.9.

In a flask, 103.5 g, corresponding to 0.1 mole of the hydroxyl group, of pentaerythritol polybehenate (I), 168.7 g corresponding to 0.1 mole of the anhydride group of the following acid anhydride-modified organopolysiloxane,

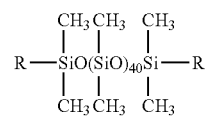

wherein R is represented by the following formula,

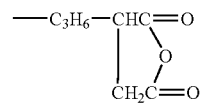

300 g of toluene and 0.3 g of potassium acetate were placed and subjected to a reaction under reflux for 4 hours. Silicone-modified esterwax (A) was obtained after toluene was removed by heat stripping at a reduced pressure. The wax (A) had a melting point of 75° C. The wax had clear appearance at temperatures above the melting point. This indicated that the wax had a uniform composition with less unreacted substances.

Preparation Example 2

Dipentaerythritol polybehenate (II) was prepared by esterification of dipentaerythritol with behenic acid, $$O(CH_2C)_2(CH_2OH)_{6-n}(CH_2OCOC_{21}H_{43})_n \qquad (II)$$

wherein n was a mixture of 3, 4, 5 and 6.

Dipentaerythritol polybehenate (II) had an OH value of 31.2 and was a mixture of dipentaerythritol hexabehenate, dipentaerythritol pentabehenate, dipentaerythritol tetrabehenate and dipentaerythritol tribehenate, whereas pure dipentaerythritol behenate has a OH value of 30.1.

Silicone-modified ester wax (B) was obtained in the same manner as in Preparation Example 1 except that 186.4 g, corresponding to 0.1 mole of the hydroxyl group, of dipentaerythritol polybehenate (II) was used in place of pentaerythritol polybehenate (I). Wax (B) had a melting point of 78° C. and clear appearance at temperatures above the melting point.

Preparation Example 3

In a flask, 107.5 g, corresponding to 0.1 mole of the double bond, of the following allylated product (III) of pentaerythritol polybehenate (I),

wherein m was a mixture of 2, 3 and 4, 143.5 g, corresponding to 0.09 mole of the SiH, of the methylhydrogenpolysiloxane having the following structure,

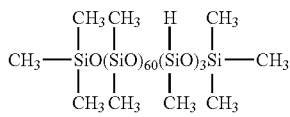

300 g of toluene, and 0.5 g of a 0.5% solution of chloroplatinic acid in toluene were placed and subjected to a reaction under reflux for 4 hours. Silicone-modified ester wax (C) was obtained after toluene was removed by heat stripping at a reduced pressure. Wax(C) had a melting point of 73° C. and clear appearance at temperatures above the melting point.

EXAMPLE 1

Milky Lotion

| (Components) | (%) |
| --- | --- |
| 1. Silicone-modified wax (A) prepared in Preparation Example 1 | 2.0 |
| 2. Dimethylpolysiloxane(6 mm²/sec, 25° C.) | 30.0 |
| 3. Decamethylcyclopentasiloxane | 10.0 |
| 4. Glyceryl trioctanoate | 5.0 |
| 5. Polyethersilicone *1 | 5.0 |
| 6. 1,3-butylene glycol | 5.0 |
| 7. Antiseptic | q.s. |
| 8. Perfume | q.s. |
| 9. Purified water | 43.0 |

*1 KF6017 (trade name, ex Shin-Etsu Chemical Co., Ltd.)

(Preparation Method)

A: Components 1-5 were heated to be a solution.

B: Components 6, 7 and 9 were mixed, to which the solution obtained in A was added and emulsified.

C: The emulsion obtained in B was cooled, to which Component 8 was added to obtain a milky lotion.

The milky lotion thus obtained was non-tacky and spread well. When applied to the skin, the milky lotion gave a glossy finish.

EXAMPLE 2

Water-in-Oil Type Cream

| (Components) | (%) |
| --- | --- |
| 1. Dimethylpolysiloxane(6 mm²/sec, 25° C.) | 10.0 |
| 2. Decamethylcyclopentasiloxane | 7.0 |
| 3. Glyceryl trioctanoate | 5.0 |
| 4. Polyether-modified branched silicone*¹ | 2.0 |
| 5. Silicone-modified wax (A) prepared in Preparation Example 1 | 1.0 |
| 6. Dipropylene glycol | 7.0 |
| 7. Antiseptic | q.s. |
| 8. Perfume | q.s. |
| 9. Purified water | 68.0 |

*¹KF6028 (trade name, ex Shin-Etsu Chemical Co., Ltd.)

(Preparation Method)

A: Components 1-5 were mixed while heating.

B: Components 6-9 were mixed, which was added to the mixture obtained in A and emulsified by stirring.

The W/O type cream thus obtained was non-tacky and spread well.

EXAMPLE 3

Water-in-Oil Type Cream

| (Components) | (%) |
| --- | --- |
| 1. Silicone-modified wax (A) prepared in Preparation Example 1 | 2.0 |
| 2. Dimethylpolysiloxane(6 mm²/sec, 25° C.) | 10.0 |
| 3. Crosslinked type polyether-modified silicone*¹ | 5.0 |
| 4. Dipropylene glycol | 10.0 |
| 5. Sodium citrate | 0.2 |
| 6. Ethanol | 5.0 |
| 7. Antiseptic | q.s. |
| 8. Perfume | q.s. |
| 9. Purified water | 67.8 |

*¹KSG-21 (trade name, ex Shin-Etsu Chemical Co., Ltd.)

(Preparation Method)

A: Components 1-3 were heated to be a solution.

B: Components 4-9 were mixed to be a solution, which was added to the solution obtained in A and emulsified by stirring.

The W/O type cream thus obtained was non-greasy and non-tacky, and spread well. It gave mat finish.

EXAMPLE 4

Water-in-Oil Type Cream Makeup Base

| (Components) | (%) |
| --- | --- |
| 1. Crosslinked type polyether-modified silicone*¹ | 4.0 |
| 2. Crosslinked type dimethylpolysiloxacone*² | 1.0 |
| 3. Polyether-modified silicone*³ | 0.5 |
| 4. Dimethylpolysiloxane(6 mm²/sec, 25° C.) | 6.0 |
| 5. Dimethylpolysiloxane(20 mm²sec, 25° C.) | 2.0 |
| 6. Decamethylcyclopentasiloxane | 3.0 |
| 7. Titanium oxide dispersion in cyclopentasiloxane*⁴ | 10.0 |
| 8. Silicone-modified wax (A) prepared in Preparation Example 1 | 1.0 |
| 9. Dipropylene glycol | 5.0 |
| 10. Sodium citrate | 0.2 |
| 11. Methyl cellulose(2% aqueous solution)*⁵ | 2.5 |
| 12. Ethanol | 3.0 |
| 13. Antiseptic | q.s. |
| 14. Perfume | q.s. |
| 15. Purified water | 61.8 |

EXAMPLE 4-continued

Water-in-Oil Type Cream Makeup Base

| (Components) | (%) |
|---|---|

*[1]KSG-21 (trade name, ex Shin-Etsu Chemical Co., Ltd.)
*[2]KSG-15 (trade name, ex Shin-Etsu Chemical Co., Ltd.)
*[3]KF-6017 (trade name, ex Shin-Etsu Chemical Co., Ltd.)
*[4]SPD-T1S (trade name, ex Shin-Etsu Chemical Co., Ltd.)
*[5]METOLOSE 65-SH4000 (trade name, ex Shin-Etsu Chemical Co., Ltd.)

(Preparation Method)
A: Components 1-8 were mixed while heating.
B: Components 9-15 were mixed to be a solution, which was added to the mixture obtained in A and emulsified by stirring.

The W/O type makeup base thus obtained was non-greasy and non-tacky, and spread well. It gave moisturized and refreshing feel and mat finish.

EXAMPLE 5

Oil-in-Water Type Cream

| (Components) | (%) |
|---|---|
| 1. Silicone-modified wax (A) prepared in Preparation Example 1 | 2.0 |
| 2. Crosslinked type dimethyl-polysiloxacone*[1] | 15.0 |
| 3. Decamethylcyclopentasiloxane | 10.0 |
| 4. Dimethylpolysiloxane(6 mm$^2$/sec, 25° C.) | 18.0 |
| 5. Polyether-modified silicone*[2] | 0.7 |
| 6. Propylene glycol | 3.0 |
| 7. Polyacrylamide mixture*[3] | 0.8 |
| 8. Xanthan gum(2% aqueous solution) | 8.0 |
| 9. Antiseptic | q.s. |
| 10. Perfume | q.s. |
| 11. Purified water | 42.5 |

*[1]KSG-16 (trade name, ex Shin-Etsu Chemical Co., Ltd.)
*[2]KF-6011 (trade name, ex Shin-Etsu Chemical Co., Ltd.)
*[3]SEPIGEL-305 (trade name, ex SEPIC Co., Ltd.)

(Preparation Method)
A: Components 1-4 were mixed while heating.
B: Components 5-11 were mixed to be a solution, which was added to the mixture obtained in A and emulsified by stirring. The O/W type cream thus obtained spread lightly on the skin and gave refreshing feel to the skin.

EXAMPLE 6

Water-in-Oil Type Solid Cream

| (Components) | (%) |
|---|---|
| 1. Silicone-modified wax (A) prepared in Preparation Example 1 | 30.0 |
| 2. Dimethylpolysiloxane(6 mm$^2$/sec, 25° C.) | 24.0 |
| 3. Decamethylcyclopentasiloxane | 24.0 |
| 4. Polyether-modified silicone*[1] | 2.0 |
| 5. 1,3-butylene glycol | 2.0 |
| 6. Antiseptic | q.s. |
| 7. Perfume | q.s. |
| 8. Purified water | 18.0 |

*[1]KF-6017 (trade name, ex Shin-Etsu Chemical Co., Ltd.)

(Preparation Method)
A: Components 1-4 were heated to be a solution.
B: Components 5-8 were mixed to be a solution, which was added to the solution obtained in A and emulsified by stirring.
C: The emulsion was placed in a container.

The W/O type cream thus obtained was non-greasy and non-tacky in spite of the large oil content. It spread well on the skin.

EXAMPLE 7

Lipstick

| (Components) | (%) |
|---|---|
| 1. Silicone-modified wax (A) prepared in Preparation Example 1 | 35.0 |
| 2. Polyethylene wax | 5.0 |
| 3. Dimethylpolysiloxane(6 mm$^2$/sec, 25° C.) | 30.0 |
| 4. Decamethylcyclopentasiloxane | 26.0 |
| 5. Acrylsilicone resin*[1] | 4.0 |
| 6. Pigment | q.s. |
| 7. Antiseptic | q.s. |
| 8. Perfume | q.s. |

*[1]KP-545 (trade name, ex Shin-Etsu Chemical Co., Ltd.)

(Preparation Method)
A: Components 1-4 were heated to be a solution.
B: Components 5-7 were mixed to be dispersion, which was added to the solution obtained in A and stirred to make a homogeneous mixture.
C: Component 8 was added to the mixture obtained in B and the mixture obtained was placed in a container.

The lipstick thus obtained was non-greasy and non-tacky. It spread lightly on the lips.

EXAMPLE 8

Powder Foundation

| (Components) | (%) |
|---|---|
| 1. Sericite | 40.0 |
| 2. Mica | 10.0 |
| 3. Talc | balance |
| 4. Titanium oxide | 10.0 |
| 5. Titanium oxide fine powder | 5.0 |
| 6. Magnesium stearate | 3.0 |
| 7. Pigment | 4.2 |
| 8. Silicone-modified wax (A) prepared in Preparation Example 1 | 1.0 |
| 9. Dimethylpolysiloxane(6 mm$^2$/sec, 25° C.) | 3.0 |
| 10. Antiseptic | q.s. |
| 11. Perfume | q.s. |

(Preparation Method)
A: Components 8-11 were mixed.
B: Components 1-7 were mixed, to which the mixture obtained in A was added and mixed homogeneously.
C: The mixture obtained in B was press-molded to make a powder foundation.

The powder foundation thus obtained was non-tacky. It spread lightly on the skin and gave a gloss finish.

EXAMPLE 9

Cream Foundation

| (Components) | (%) |
|---|---|
| 1. Crosslinked type polyether-modified silicone*[1] | 4.0 |
| 2. Glyceryl trioctanoate | 3.0 |
| 3. Dimethylpolysiloxane(6 mm$^2$/sec, 25° C.) | 5.0 |
| 4. Decamethylcyclopentasiloxane | 6.0 |

EXAMPLE 9-continued

Cream Foundation

| (Components) | (%) |
|---|---|
| 5. Silicone-modified wax (A) prepared in Preparation Example 1 | 2.0 |
| 6. Fluorine-modified hybrid silicone composite powder[*2] | 2.5 |
| 7. Pigment | 8.0 |
| 8. Acryl silicone resin[*3] | 5.0 |
| 9. Dipropylene glycol | 5.0 |
| 10. Sodium citrate | 0.2 |
| 11. Antiseptic | q.s. |
| 12. Perfume | q.s. |
| 13. Purified water | 59.3 |

[*1]KSG-21 (trade name, ex Shin-Etsu Chemical Co., Ltd.)
[*2]KSP-200 (trade name, ex Shin-Etsu Chemical Co., Ltd.)
[*3]KP-545 (trade name, ex Shin-Etsu Chemical Co., Ltd.)

(Preparation Method)
A: Components 1-6 were mixed while heating.
B: Components 9-13 were mixed to be a solution, which was added to the mixture obtained in A and emulsified by stirring.
C: Components 7 and 8 were mixed, which was added to the emulsion obtained in B and made homogeneous.

The cream foundation thus obtained was non-tacky. It spread well on the skin and gave mat finish.

EXAMPLE 10

Solid Foundation

| (Components) | (%) |
|---|---|
| 1. Silicone-modified wax (A) prepared in Preparation Example 1 | 30.0 |
| 2. Polyethylene wax | 5.0 |
| 3. Dimethylpolysiloxane(6 mm$^2$/sec, 25° C.) | 32.5 |
| 4. Decamethylcyclopentasiloxane | 28.5 |
| 5. Acrylic silicone resin[*1] | 4.0 |
| 6. Pigment | q.s. |
| 7. Antiseptic | q.s. |
| 8. Perfume | q.s. |

[*1]KP-545 (trade name, ex Shin-Etsu Chemical Co., Ltd.)

(Preparation Method)
A: Components 1-4 were heated to be a solution.
B: Components 5-7 were mixed to be dispersion, which was added to the solution obtained in A and stirred to make a homogeneous mixture.
C: Component 8 was added to the mixture obtained in B and the mixture obtained was placed in a container.

The foundation thus obtained was non-greasy and non-tacky. It spread lightly on the skin.

EXAMPLE 11

Water-in-oil Type Compact Foundation

| (Components) | (%) |
|---|---|
| 1. Silicone-modified wax (A) prepared in Preparation Example 1 | 25.0 |
| 2. Candellila wax | 5.0 |
| 3. Dimethylpolysiloxane(6 mm$^2$/sec, 25° C.) | 24.0 |
| 4. Decamethylcyclopentasiloxane | 22.0 |
| 5. Acrylic silicone resin[*1] | 4.0 |
| 6. Trimethylsiloxy silicic acid[*2] | 1.0 |
| 7. Polyether-modified silicone[*3] | 2.0 |
| 8. Pigment | q.s. |

EXAMPLE 11-continued

Water-in-oil Type Compact Foundation

| (Components) | (%) |
|---|---|
| 9. 1,3-butylene glycol | 2.0 |
| 10. Antiseptic | q.s. |
| 11. Perfume | q.s. |
| 12. Purified water | 15.0 |

[*1]KP-545 (trade name, ex Shin-Etsu Chemical Co., Ltd.)
[*2]KF-7312J (trade name, ex Shin-Etsu Chemical Co., Ltd.)
[*3]KF-6017 (trade name, ex Shin-Etsu Chemical Co., Ltd.)

(Preparation Method)
A: Components 1-4, and 7 were heated to be a solution.
B: Components 9,10 and 12 were mixed to be a solution, which was added to the solution obtained in A and emulsified by stirring.
C: Components 5,6 and 8 were mixed to be dispersion, which was added to the emulsion obtained in B.
D: Component 11 was added to the mixture obtained in C, which was placed in a container.

The W/O type compact foundation thus obtained was non-greasy and non-sticky in spite of the large oil content. It spread well on the skin.

EXAMPLE 12

Eye Shadow

| (Components) | (%) |
|---|---|
| 1. Sericite | 40.0 |
| 2. Mica | 10.0 |
| 3. Talc | balance |
| 4. Titanium oxide | 10.0 |
| 5. Titanium oxide fine powder | 5.0 |
| 6. Magnesium stearate | 3.0 |
| 7. Pigment | q.s. |
| 8. Octyldecanol | 3.0 |
| 9. Dimethylpolysiloxane(6 mm$^2$/sec, 25° C.) | 8.0 |
| 10. Silicone-modified wax (B) prepared in Preparation Example 2 | 2.0 |
| 10. Antiseptic | q.s. |
| 11. Perfume | q.s. |

(Preparation Method)
A: Components 8-11 were mixed while heating.
B: Components 1-7 were mixed, to which the mixture obtained in A were added and made homogeneous.
C: Component 14 was added to the mixture obtained in B.

The eye shadow thus obtained was non-greasy and spread well on the eyelids to give a glossy finish.

EXAMPLE 13

Powder Eyebrow

| (Components) | (%) |
|---|---|
| 1. Silicone-modified wax (B) prepared in Preparation Example 2 | 3.0 |
| 2. Dimethylpolysiloxane(6 mm$^2$/sec, 25° C.) | 5.0 |
| 3. Glyceryl trioctanoate | 2.0 |
| 4. Silicone-treated mica | 40.0 |
| 5. Silicone-treated barium sulfate | 15.0 |
| 6. Silicone-treated titanium oxide | 10.0 |
| 7. Silicone-treated pigment | q.s. |
| 8. Hybrid silicone composite powder[*1] | 1.5 |
| 9. Spherical polymethylsilsesquioxane powder[*2] | 2.5 |
| 10. Silicone-treated talc | balance |

EXAMPLE 13-continued

Powder Eyebrow

| (Components) | (%) |
|---|---|
| 11. Antiseptic | q.s. |
| 12. Perfume | q.s. |

*[1] KSP-100 (trade name, ex Shin-Etsu Chemical Co., Ltd.)
*[2] KMP-590 (trade name, ex Shin-Etsu Chemical Co., Ltd.)

(Preparation Method)
A: Components 4-12 were mixed to be homogeneous.
B: Components 1-3 were mixed to be a solution, which was added to the mixture obtained in A and made homogeneous.
C: The mixture obtained in B was press molded in a metal mold to prepare powder eyebrow.

The eyebrow thus obtained was non-tacky and spread well to give a glossy finish.

EXAMPLE 14

Eyebrow Pencil

| (Components) | (%) |
|---|---|
| 1. Silicone-modified wax (B) prepared in Preparation Example 2 | 40.0 |
| 2. polyethylene wax | 10.0 |
| 3. Dimethylpolysiloxane(6 mm$^2$/sec, 25° C.) | 40.0 |
| 4. Decamethylcyclopentasiloxane | 5.0 |
| 5. Acrylic silicone resin*[1] | 5.0 |
| 6. Pigment | q.s. |
| 7. Antiseptic | q.s. |
| 8. Perfume | q.s. |

*[1] KP-545 (trade name, ex Shin-Etsu Chemical Co., Ltd.)

(Preparation Method)
A: Components 1-4 were mixed to be a solution.
B: Components 5-7 were mixed to be dispersion, which was added to the solution obtained in A and made homogeneous.
C: Component 8 was added to the mixture obtained in B, which was placed in a container.

The eyebrow pencil thus obtained was not floury. It was lubricious, and spread well.

EXAMPLE 15

Hair Cream

| (Components) | (%) |
|---|---|
| 1. Silicone-modified wax (B) prepared in Preparation Example 2 | 2.0 |
| 2. Dimethylpolysiloxane(6 mm$^2$/sec, 25° C.) | 5.0 |
| 3. Decamethylcyclopentasiloxane | 8.0 |
| 4. Stearyltrimethylammonium chloride | 1.5 |
| 5. Glycerin | 3.0 |
| 6. Propylene glycol | 5.0 |
| 7. Hydroxyethylcellulose | 0.2 |
| 8. Antiseptic | q.s. |
| 9. Perfume | q.s. |
| 10. Purified water | 75.3 |

(Preparation Method)
A: Components 1-3 were mixed to be a solution.
B: Components 4-8 and 10 were mixed to be a homogeneous solution.
C: The solution obtained in B was added to the solution from A and emulsified. The emulsion was cooled, to which Component 9 was added.

The hair cream thus obtained spread well on the hair and gave softness, smoothness, moisturized feel and gloss to the hair.

EXAMPLE 16

Conditioning Mousse

| (Components) | (%) |
|---|---|
| 1. Silicone-modified wax (B) prepared in Preparation Example 2 | 0.5 |
| 2. Dimethylpolysiloxane(6 mm$^2$/sec, 25° C.) | 2.0 |
| 3. Crosslinked dimethylpolysiloxane*[1] | 0.5 |
| 4. Glyceryl trioctanoate | 1.5 |
| 5. Glycerin | 3.0 |
| 6. Stearyldimethylbenzylammonium chloride | 0.5 |
| 7. Polyoxyethylene hydrogenated castor oil | 0.5 |
| 8. Ethanol | 7.0 |
| 9. Antiseptic | q.s. |
| 10. Perfume | q.s. |
| 11. Purified water | Balance |
| 12. Liquefied petroleum gas | 5.0 |

*[1] KSG-16 (trade name, ex Shin-Etsu Chemical Co., Ltd.)

(Preparation Method)
A: Components-1-4 were mixed to be a solution.
B: Components 5-9 and 11 were mixed to be a homogeneous solution.
C: The solution obtained in B was added to the solution from A and emulsified. The emulsion was cooled, to which Component 10 was added.
D: The product from C was placed in an aerosol can to prepare a conditioning mousse.

The conditioning mousse thus obtained gave moisturized, soft and smooth feel to the hair. It was non-greasy to give mat finish.

EXAMPLE 17

Roll-On Type Antiperspirant

| (Components) | (%) |
|---|---|
| 1. Silicone-modified wax (B) prepared in Preparation Example 2 | 5.0 |
| 2. Crosslinked polyether-modified silicone*[1] | 20.0 |
| 3. Dimethylpolysiloxane(6 mm$^2$/sec, 25° C.) | 10.0 |
| 4. Crosslinked dimethylpolysiloxane*[2] | 15.0 |
| 5. Decamethylcyclopentasiloxane | 30.0 |
| 6. Aluminum zirconium tetrachlorohydrate | 20.0 |
| 7. Perfume | q.s. |

*[1] KSG-21 (trade name, ex Shin-Etsu Chemical Co., Ltd.)
*[2] KSG-15 (trade name, ex Shin-Etsu Chemical Co., Ltd.)

(Preparation Method)
A: Components 1-5 were mixed while heating.
B: Components 6 and 7 were added to the mixture obtained in A and dispersed homogeneously.

The roll-on antiperspirant thus obtained spread well on the skin. It was non-greasy, non-tacky and stable with temperature and time.

EXAMPLE 18

Water-in-Oil Antiperspirant

| (Components) | (%) |
|---|---|
| 1. Silicone-modified wax (B) prepared in Preparation Example 2 | 2.0 |
| 2. Crosslinked polyether-modified silicone[*1] | 7.0 |
| 3. Decamethylcyclopentasiloxane | 7.0 |
| 4. Glyceryl trioctanoate | 8.0 |
| 5. 1,3-butylene glycol | 5.0 |
| 6. Sodium citrate | 0.2 |
| 7. Aluminum chlorohydrate | 20.0 |
| 8. Perfume | q.s. |
| 9. Purified water | 50.8 |

[*1]KSG-21 (trade name, ex Shin-Etsu Chemical Co., Ltd.)

(Preparation Method)
A: Components 1-4 were mixed while heating.
B: Components 5,6 and 8 were mixed, to which Components 7 and 8 were added and dissolved.
C: To the mixture obtained in A, the mixture obtained in B was added and emulsified by stirring.

The W/O antiperspirant thus obtained spread well on the skin. It was non-greasy, non-tacky and stable with temperature and time.

EXAMPLE 19

Solid antiperspirant

| (Components) | (%) |
|---|---|
| 1. Silicone-modified wax (A) prepared in Preparation Example 1 | 22.0 |
| 2. Polyethylene/polypropylene copolymer | 4.0 |
| 3. Dimethylpolysiloxane(6 mm$^2$/sec, 25° C.) | 22.0 |
| 4. Decamethylcyclopentasiloxane | 22.0 |
| 5. Crosslinked dimethylpolysiloxane[*1] | 15.0 |
| 6. Aluminum zirconium tetrachlorohydrate | 15.0 |
| 7. Perfume | q.s. |

[*1]KSG-16 (trade name, ex Shin-Etsu Chemical Co., Ltd.)

(Preparation Method)
A: Components 1-5 were heated to be a homogeneous mixture.
B: Components 6 and 7 were added to the mixture obtained in A and dispersed.
C: The dispersion obtained in B was placed in a container.

The solid antiperspirant thus obtained spread well on the skin. It was non-greasy, non-tacky and stable with temperature and time.

EXAMPLE 20

Solid Antiperspirant

| (Components) | (%) |
|---|---|
| 1. Silicone-modified wax (B) prepared in Preparation Example 2 | 25.0 |
| 2. Polyethylene wax | 8.0 |
| 3. Dimethylpolysiloxane(6 mm$^2$/sec, 25° C.) | 25.0 |
| 4. Decamethylcyclopentasiloxane | 22.0 |
| 5. Crosslinked dimethylpolysiloxane[*1] | 5.0 |
| 6. Aluminum zirconium tetrachlorohydrate(glycine salt) | 15.0 |
| 7. Perfume | q.s. |

[*1]KSG-16 (trade name, ex Shin-Etsu Chemical Co., Ltd.)

(Preparation Method)
A: Components 1-5 were heated to be a homogeneous mixture.
B: Components 6 and 7 were added to the mixture obtained in A and dispersed.
C: The dispersion obtained in B was placed in a container.

The solid antiperspirant thus obtained spread well on the skin. It was non-greasy, non-tacky and stable with temperature and time.

EXAMPLE 21

UV-ray Protective Water-in-Oil Type Cream

| (Components) | (%) |
|---|---|
| 1. Silicone-treated zinc oxide | 20.0 |
| 2. Acryl-modified silicone resin[*1] | 12.0 |
| 3. Decamethylcyclopentasiloxane | 20.0 |
| 4. Glyceryl trioctanoate | 3.0 |
| 5. Silicone-modified wax (C) prepared in Preparation Example 3 | 2.0 |
| 6. Crosslinked polyether-modified silicone[*2] | 5.0 |
| 7. Polyether-modified silicone[*3] | 1.0 |
| 8. Alkyl- and polyether-modified silicone[*4] | 1.0 |
| 9. Methoxy octylcinnamate | 6.0 |
| 10. Sodium citrate | 0.2 |
| 11. Dipropylene glycol | 3.0 |
| 12. Antiseptic | q.s. |
| 13. Perfume | q.s. |
| 14. Purified water | 26.8 |

[*1]KP-545 (trade name, ex Shin-Etsu Chemical Co., Ltd.)
[*2]KSG-21 (trade name, ex Shin-Etsu Chemical Co., Ltd.)
[*3]KF-6017 (trade name, ex Shin-Etsu Chemical Co., Ltd.)
[*4]KF-6026 (trade name, ex Shin-Etsu Chemical Co., Ltd.)

(Preparation Method)
A: A part of Component 3 and Components 4-9 were mixed while heating.
B: Components 10-12 and 14 were mixed, which was added to the mixture obtained in A, and emulsified by stirring.
C: Components 1, 2 and the rest of Component 3 were mixed and added to the emulsion obtained in B, to which Component 13 was added.

The W/O type UV-ray protective cream thus obtained spread well on the skin. It was transparent, non-greasy, non-tacky and stable with temperature and time.

EXAMPLE 22

UV-ray Protective Water-in-Oil Cream

| (Components) | (%) |
|---|---|
| 1. Dimethylpolysiloxane(6 mm$^2$/sec, 25° C.) | 5.0 |
| 2. Crosslinked polyether-modified silicone[*1] | 5.0 |
| 3. Glyceryl trioctanoate | 2.0 |
| 4. Silicone-modified wax (C) prepared in Preparation Example 3 | 1.0 |
| 5. Polyether-modified silicone[*2] | 1.0 |
| 6. Dispersion of titanium oxide in decamethylcyclopentasiloxane[*3] | 30.0 |
| 7. Dispersion of zinc oxide in decamethylcyclopentasiloxane[*4] | 30.0 |
| 8. Dipropylene glycol | 3.0 |
| 9. Sodium citrate | 0.2 |
| 10. Antiseptic | q.s. |
| 11. Perfume | q.s. |
| 12. Purified water | 22.8 |

[*1]KSG-21 (trade name, ex Shin-Etsu Chemical Co., Ltd.)
[*2]KF-6071 (trade name, ex Shin-Etsu Chemical Co., Ltd.)
[*3]SPD-T1S (trade name, ex Shin-Etsu Chemical Co., Ltd.)
[*4]SPD-Z1 (trade name, ex Shin-Etsu Chemical Co., Ltd.)

(Preparation Method)

A: Components 1-5 were mixed while heating.
B: Components 8-10 and 12 were mixed to be a solution, which was added to the mixture obtained in A, and emulsified by stirring.
C: Components 6, 7 and 11 were added to the emulsion obtained in B and made homogeneous.

The W/O type UV-ray protective cream thus obtained spread well on the skin. It was transparent, non-greasy and non-tacky. It was stable with temperature and time.

EXAMPLE 23

UV-ray Protective Oil-in-Water Type Cream

| (Components) | (%) |
|---|---|
| 1. Crosslinked organopolysiloxane*$^1$ | 5.0 |
| 2. Cetyl isooctanoate | 5.0 |
| 3. Silicone-modified wax (C) prepared in Preparation Example 3 | 1.0 |
| 4. Dispersion of titanium oxide in decamethylcyclopentasiloxane*$^3$ | 15.0 |
| 5. Polyether-modified silicone*$^3$ | 1.0 |
| 6. Polyether-modified silicone*$^4$ | 1.0 |
| 7. Acrylic acid amide mixture*$^5$ | 2.0 |
| 8. Propylene glycol | 5.0 |
| 9. Methylcellulose (2% aqueous solution)*$^6$ | 5.0 |
| 10. Antiseptic | q.s. |
| 11. Perfume | q.s. |
| 12. Purified water | 60.0 |

*$^1$KSG-18 (trade name, ex Shin-Etsu Chemical Co., Ltd.)
*$^2$SPD-T1S (trade name, ex Shin-Etsu Chemical Co., Ltd.)
*$^3$KF-6027 (trade name, ex Shin-Etsu Chemical Co., Ltd.)
*$^4$KF-6011 (trade name, ex Shin-Etsu Chemical Co., Ltd.)
*$^5$SEPIGEL-305 (trade name, ex SEPPIC Co., Ltd.)
*$^6$METOLOSE SM-4000 (trade name, ex Shin-Etsu Chemical Co., Ltd.)

(Preparation Method)

A: Components 5-8, 10 and 12 were mixed.
B: Components 1-3 were mixed while heating, which was added to the mixture obtained in A, and emulsified by stirring.
C: Component 4 was added to the emulsion obtained in B, to which Components 9 and 10 were added and made homogeneous.

The O/W UV-ray protective cream thus obtained spread well on the skin. It was transparent, non-greasy and non-tacky. It was stable with temperature and time.

Comparative Example 1: Solid Foundation

A solid foundation was prepared according to the procedures in Example 10 except that the silicone wax represented by the following formula was used in place of Component 1, silicone-modified wax.

$$(CH_3)_3SiO(SiO)_m(SiO)_nSi(CH_3)_3$$
with side groups $CH_3$ and $(CH_2)_3-OC(CH_2)_{20}CH_3$ (C=O)

In the above formula, m is 2 or 3, n is an integer of from 13 to 15, and the silicone wax has a melting point of from 45 to 53° C.

The solid foundation obtained was tackier and worse in spreading property than the foundation in Example 10.

Comparative Example 2: Solid Foundation

A solid foundation was prepared according to the procedures in Example 10 except that the silicone wax prepared by the method described below was used in place of Component 1, silicone-modified wax.

Thirty grams of the following dimethylpolysiloxane having a methacrylate substituent at one end, $$CH_2=CCOO(CH_2)_3SiO(SiO)_{50}Si(CH_3)_3$$
with $CH_3$ group on the carbonyl carbon and $CH_3CH_3$ / $CH_3CH_3$ side groups 30 g of methymethacrylate, 40 g of n-butylmethacrylate, and 100 g of toluene were mixed, to which 1.5 g of azobisisobutylonitrile was added and dissolved. Then, a reaction was carried out at a temperature of from 80 to 90 ° C. for 5 hours. A viscous solution thus obtained was poured in 2-liter of methanol to precipitate a graft polymer. The polymer was isolated by filtering and dried. A white acryl-silicone graft copolymer wax was obtained which had a weight average molecular weight, reduced to polystyrene, determined by GPC of 16,000 and a glass transition temperature of 18° C.

The solid foundation obtained lacked lubricity and did not spread smoothly.

INDUSTRIAL APPLICABILITY

The present cosmetic comprising silicone-modified wax has good spreadability and good sensory properties with refreshing feel of silicone oil. The present composition is suitable for preparing a cosmetic which spread smoothly and gives a refreshing feel.

The invention claimed is:

1. A cosmetic comprising;
an organopolysiloxane wax represented by the following formula (1), $$R^1_{3-r}\text{—SiO}\underset{R^2_r}{\overset{}{|}}\text{—}(\text{SiO})_p\underset{R^1}{\overset{R^1}{|}}(\text{SiO})_q\underset{R^1}{\overset{R^2}{|}}\text{—Si}\underset{}{\overset{R^2_s}{|}}\text{—}R^1_{3-s} \quad (1)$$

wherein $R^1$ is a group selected from the group consisting of alkyl groups having 1 to 20 carbon atoms, alicyclic groups, aryl groups, aralkyl groups and fluorinated alkyl groups;
$R^2$ is a group having a pentaerythritol higher fatty acid polyester residue represented by the following formula (2), $$(CH_2OCOR^8)_mC(CH_2OH)_{3-m}(CH_2O\text{—}X\text{—}) \quad (2)$$

wherein $1 \leq m < 4$,
or a group having a dipentaerythriol higher fatty acid polyester residue represented by the following formula (3), $$O(CH_2C)_2(CH_2OCO\,R^8)_n(CH_2OH)_{5-n}(CH_2O\text{—}X\text{—}) \quad (3)$$

wherein $1 \leq n < 6$,
$R^8$ in the formulae (2) and (3) being a linear, saturated or unsaturated, aliphatic group having 17 to 30 carbon atoms, —X— in the formulae (2) and (3) being any one of the following moieties,

—R³—,

—COR⁴—, wherein R³ is a C₃-C₈ alkylene group or a cycloalkylene group, R⁴ is a C₄-C₂₀ aliphatic or alicyclic group having at least one group selected from the group consisting of carboxyl, carbonyloxy and hydroxyl groups, p, q, r and s each is a number with $0 \leq p \leq 200$, $0 \leq q \leq 200$, $0 \leq r \leq 3$, and $0 \leq s \leq 3$, provided that $0 \leq p+q \leq 200$ and $1 \leq q+r+s$; and (a) a silicone oil which is liquid at 25° C. in an amount of from 1 to 70 wt % based on a total weight of the cosmetic.

2. The cosmetic according to claim 1, wherein R⁴ is any one of the following moieties,

—CH(CH₂COOH)—R⁵—,

—R⁶COOC(OH)R⁷—, wherein R⁵ is a C₃-C₈ alkylene or cycloalkylene group, R⁶ is a C₃-C₈ alkylene group, and R⁷ is a C₃-C₈ alkylene or cycloalkylene group.

3. The cosmetic according to claim 1, wherein the organopolysiloxane wax has a weight average molecular weight, reduced to polystyrene, of from 1,000 to 8,000.

4. The cosmetic according to claim 1, wherein the silicone oil (a) is at least one selected from the group consisting of linear organopolysiloxanes represented by the following formula (7), cyclic organopolysiloxanes represented by the following formula (8) and branched organopolysiloxanes represented by the following formula (9),

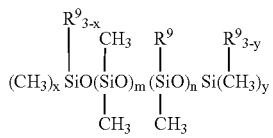

(7)

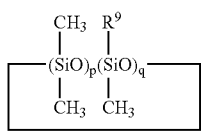

(8)

(CH₃)₄₋ᵣSi{OSi(CH₃)₃}ᵣ (9)

wherein R⁹ is selected from the group consisting of a hydrogen atom, a hydroxyl group, unsubstituted or fluorinated alkyl groups having 1 to 20 carbon atoms, aryl groups, amino-substituted alkyl groups, alkoxy groups and a group represented by the formula, (CH₃)₃SiO{(CH₃)₂SiO}ₛSi(CH₃)₂CH₂CH₂—, wherein m is an integer of from 0 to 1000, n is an integer of from 0 to 1000, with m+n ranging from 1 to 1000, x and y each is 0, 1, 2 or 3, p each is an integer of from 0 to 8 with $3 \leq p+q \leq 8$, r is an integer of from 1 to 4 and s is an integer of from 0 to 500.

5. The cosmetic according to claim 4, wherein the silicone oil (a) is a dimethylpolysiloxane having a viscosity of from 1 to 30 mm²/s at 25° C.

6. The cosmetic according to claim 4, wherein the silicone oil (a) is decamethylcyclopentasiloxane.

7. The cosmetic according to claim 1, wherein the silicone oil (a) is a crosslinked organopolysiloxane swollen with a silicone oil having a viscosity of from 0.65 to 10.0 mm²/s in an amount larger than or equal to the weight of the crosslinked organopolysiloxane itself.

8. The cosmetic according to claim 7, wherein the crosslinked organopolysiloxane has at least one moiety selected from the group consisting of polyoxyalkylene, polyglycerin, alkyl, alkenyl, aryl, and fluoroalkyl moieties.

9. The cosmetic according to claim 1, wherein the silicone oil (a) is an acrylic silicone resin dissolved in a volatile silicone, a volatile hydrocarbon oil, a non-volatile silicone, or a non-volatile hydrocarbon oil, said acrylic silicone resin being semisolid or solid at room temperature.

10. The cosmetic according to claim 9, wherein the acrylic silicone resin has at least one moiety selected from the group consisting of pyrrolidone, long alkyl chains, polyoxyalkylene, and fluoroalkyl moieties.

11. The cosmetic according to claim 1, wherein the silicone oil (a) is a gummy linear silicone dissolved in decamethylcyclopentasiloxane, said gummy linear silicone being represented by the formula, (CH₃)₃SiO{(CH₃)₂SiO}ₜ{(CH₃)R¹⁰SiO}ᵤSi(CH₃)₃, wherein R¹⁰ is selected from the group consisting of alkyl groups having 6 to 20 carbon atoms, amino-substituted alkyl groups having 3 to 15 carbon atoms, fluorinated alkyl groups, alkyl groups having quarterly ammonium group, t ranges from 1001 to 20000, and u ranges from 0 to 5000 with t+u ranging from 1001 to 25000.

12. The cosmetic according to claim 1, wherein the silicone oil (a) is a silicone network compound dissolved in decamethylcyclopentasiloxane, said silicone network compound being selected from the group consisting of silicone network compounds represented by MQ, MDQ, MT, MDT, or MDTQ and silicone network compounds having at least one moiety selected from the group consisting of pyrrolidone, long alkyl chains, polyoxyalkylene, fluoroalkyl and amino moieties.

13. A cosmetic comprising:
an organopolysiloxane wax represented by the following formula (1),

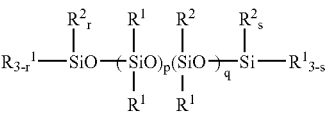

(1)

wherein R¹ is a group selected from the group consisting of alkyl groups having 1 to 20 carbon atoms, alicyclic groups, aryl groups, aralkyl groups and fluorinated alkyl groups;

R² is a group having a pentaerythritol higher fatty acid polyester residue represented by the following formula (2), (CH₂OCOR⁸)ₘC(CH₂OH)₃₋ₘ(CH₂O—X—) (2)

wherein $1 \leq m < 4$, or a group having a dipentaerythritol higher fatty acid polyester residue represented by the following formula (3),

O(CH₂C)₂(CH₂OCOR⁸)ₙ(CH₂OH)₅₋ₙ(CH₂O—X—) (3)

wherein $1 \leq n < 6$,

R⁸ in the formulae (2) and (3) being a linear, saturated or unsaturated, aliphatic group having 17 to 30 carbon atoms, —X— in the formulae (2) and (3) being any one of the following moieties,

—R³—,

—COR⁴—, wherein R³ is a $C_3$-$C_8$ alkylene group or a cycloalkylene group, R⁴ is a $C_4$-$C_{20}$ aliphatic or alicyclic group having at least one group selected from the group consisting of carboxyl, carbonyloxy and hydroxyl groups, p, q, r and s each is a number with $0 \leq p \leq 200$, $0 \leq q \leq 200$, $0 \leq r \leq 3$, and $0 \leq s \leq 3$, provided that $0 \leq p+q \leq 200$ and $1 \leq q+r+s$; and (b) an unctuous agent, except silicone oils, in an amount of from 5 to 95 wt % based on a total weight of the cosmetic.

14. The cosmetic according to claim 13, wherein at least a part of the unctuous agent (b) is a solid unctuous agent having a melting point of 50° C. or higher.

15. A cosmetic comprising:
an organopolysiloxane wax represented by the following formula (1),

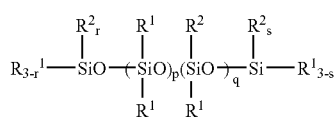  (1)

wherein R¹ is a group selected from the group consisting of alkyl groups having 1 to 20 carbon atoms, alicyclic groups, aryl groups, aralkyl groups and fluorinated alkyl groups;

R² is a group having a pentaerythritol higher fatty acid polyester residue represented by the following formula (2),

  (2)

wherein $1 \leq m < 4$, or a group having a dipentaerythritol higher fatty acid polyester residue represented by the following formula (3),

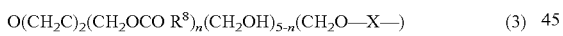  (3)

wherein $1 \leq n < 6$,

R⁸ in the formulae (2) and (3) being a linear, saturated or unsaturated, aliphatic group having 17 to 30 carbon atoms, —X— in the formulae (2) and (3) being any one of the following moieties,

—R³—,

—COR⁴—, wherein R³ is a $C_3$-$C_8$ alkylene group or a cycloalkylene group, R⁴ is a $C_4$-$C_{20}$ aliphatic or alicyclic group having at least one group selected from the group consisting of carboxyl, carbonyloxy and hydroxyl groups, p, q, r and s each is a number with $0 \leq p \leq 200$, $0 \leq q \leq 200$, $0 \leq r \leq 3$, and $0 \leq s \leq 3$, provided that $0 \leq p+q \leq 200$ and $1 \leq q+r+s$; and (c) a compound having an alcoholic hydroxyl group.

16. A cosmetic comprising:
an organopolysiloxane wax represented by the following formula (1),

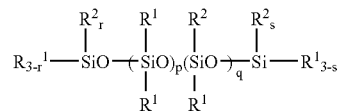  (1)

wherein R¹ is a group selected from the group consisting of alkyl groups having 1 to 20 carbon atoms, alicyclic groups, aryl groups, aralkyl groups and fluorinated alkyl groups;

R² is a group having a pentaerythritol higher fatty acid polyester residue represented by the following formula (2),

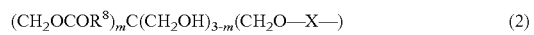  (2)

wherein $1 \leq m < 4$, or a group having a dipentaerythritol higher fatty acid polyester residue represented by the following formula (3),

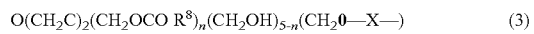  (3)

wherein $1 \leq n < 6$,

R⁸ in the formulae (2) and (3) being a linear, saturated or unsaturated, aliphatic group having 17 to 30 carbon atoms, —X— in the formulae (2) and (3) being any one of the following moieties,

—R³—,

—COR⁴—, wherein R³ is a $C_3$-$C_8$ alkylene group or a cycloalkylene group, R⁴ is a $C_4$-$C_{20}$ aliphatic or alicyclic group having at least one group selected from the group consisting of carboxyl, carbonyloxy and hydroxyl groups, p, q, r and s each is a number with $0 \leq p \leq 200$, $0 \leq q \leq 200$, $0 \leq r \leq 3$, and $0 \leq s \leq 3$, provided that $0 \leq p+q \leq 200$ and $1 \leq q+r+s$; and (d) water.

17. A cosmetic comprising:
an organopolysiloxane wax represented by the following formula (1),

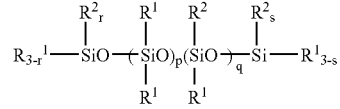  (1)

wherein R¹ is a group selected from the group consisting of alkyl groups having 1 to 20 carbon atoms, alicyclic groups, aryl groups, aralkyl groups and fluorinated alkyl groups;

R² is a group having a pentaerythritol higher fatty acid polyester residue represented by the following formula (2),

  (2)

wherein $1 \leq m < 4$, or a group having a dipentaerythritol higher fatty acid polyester residue represented by the following formula (3),

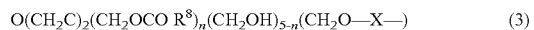  (3)

wherein 1≦n<6, $R^8$ in the formulae (2) and (3) being a linear, saturated or unsaturated, aliphatic group having 17 to 30 carbon atoms, —X— in the formulae (2) and (3) being any one of the following moieties,

—$R^3$—,

—$COR^4$—, wherein $R^3$ is a $C_3$-$C_8$ alkylene group or a cycloalkylene group, $R^4$ is a $C_4$-$C_{20}$ aliphatic or alicyclic group having at least one group selected from the group consisting of carboxyl, carbonyloxy and hydroxyl groups, p, q, r and s each is a number with 0≦p≦200, 0≦q≦200, 0≦r≦3, and 0≦s≦3, provided that 0≦p+q≦200 and 1≦q+r+s; and (e) powder and/or a pigment.

18. The cosmetic according to claim 17, wherein at least a part of the powder and/or a pigment (e) is crosslinked dimethylsilicone fine powder, polymethylsilsesquioxane fine powder, silica treated to become hydrophobic, or composite fine powder of spherical silicone rubber coated with polymethylsilsesquioxane particles.

19. A cosmetic comprising:

an organopolysiloxane wax represented by the following formula (1),

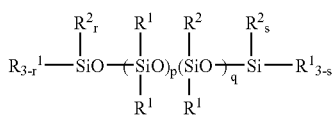

wherein $R^1$ is a group selected from the group consisting of alkyl groups having 1 to 20 carbon atoms, alicyclic groups, aryl groups, aralkyl groups and fluorinated alkyl groups;

$R^2$ is a group having a pentaerythritol higher fatty acid polyester residue represented by the following formula (2), $(CH_2OCOR^8)_mC(CH_2OH)_{3-m}(CH_2O—X—)$      (2)

wherein 1≦m<4, or a group having a dipentaerythritol higher fatty acid polyester residue represented by the following formula (3), $O(CH_2C)_2(CH_2OCOR^8)_n(CH_2OH)_{5-n}(CH_2O—X—)$      (3)

wherein 1≦n <6, $R^8$ in the formulae (2) and (3) being a linear, saturated or unsaturated, aliphatic group having 17 to 30 carbon atoms, —X— in the formulae (2) and (3) being any one of the following moieties,

—$R^3$—,

—$COR^4$—, wherein $R^3$ is a $C_3$-$C_8$ alkylene group or a cycloalkylene group, $R^4$ is a $C_4$-$C_{20}$ aliphatic or alicyclic group having at least one group selected from the group consisting of carboxyl, carbonyloxy and hydroxyl groups, p, q, r and s each is a number with 0≦p≦200, 0≦q≦200, 0≦r≦3, and 0≦s≦3, provided that 0≦p+q≦200 and 1≦q+r+s; and (f) a surfactant.

20. The cosmetic according to claim 19, wherein the surfactant (f) is at least one selected from the group consisting of polyoxyalkylene-modified organopolysiloxanes, polyglycerin-modified organopolysiloxanes and polyalkylene and alkyl-modified organopolysiloxanes.

21. The cosmetic according to claim 1, wherein the cosmetic is in the form of liquid, milky lotion, cream, solid, paste, gel, multilayer, mousse, spray or stick.

22. The cosmetic according to claim 1, wherein the cosmetic is a skin care cosmetic, hair cosmetic, antiperspirant, makeup cosmetic, or UV-ray protective cosmetic.

23. A composition comprising:

an organopolysiloxane wax represented by the following formula (1)

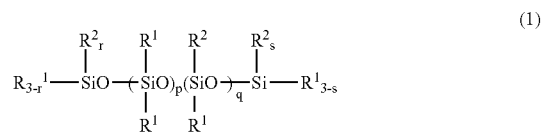

wherein $R^1$ is a group selected from the group consisting of alkyl groups having 1 to 20 carbon atoms, alicyclic groups, aryl groups, aralkyl groups and fluorinated alkyl groups;

$R^2$ is a group having a pentaerythritol higher fatty acid polyester residue represented by the following formula (2), $(CH_2OCOR^8)_mC(CH_2OH)_{3-m}(CH_2O—X—)$      (2)

wherein 1≦m≦4, or a group having a dipentaerythritol higher fatty acid polyester residue represented by the following formula (3), $O(CH_2C)_2(CH_2OCO\ R^8)_n(CH_2OH)_{5-n}(CH_2O—X—)$      (3)

wherein 1≦n<6, $R^8$ in the formulae (2) and (3) being a linear, saturated or unsaturated, aliphatic group having 17 to 30 carbon atoms, —X— in the formulae (2) and (3) being any one of the following moieties,

—$R^3$—,

—$COR^4$—, wherein $R^3$ is a $C_3$-$C_8$ alkylene group or a cycloalkylene group, $R^4$ is a $C_4$-$C_{20}$ aliphatic or alicyclic group having at least one group selected from the group consisting of carboxyl, carbonyloxy and hydroxyl groups, p, q, r and s each is a number with 0≦p≦200, 0≦q≦200, 0≦r≦3, and 0≦s≦3, provided that 0≦p+q≦200 and 1≦q+r+s; and a silicone unctuous agent which is liquid at 25° C. in a weight ratio of from 1:0.01 to 1:45.

24. The composition according to claim 23, wherein the composition comprises the organopolysiloxane wax represented by the formula (1) and the silicone unctuous agent which is liquid at 25° C. in a weight ratio of from 1:0.5 to 1:20.

* * * * *